(12) United States Patent
Fojtik (10) Patent No.: US 11,357,408 B2
(45) Date of Patent: Jun. 14, 2022

(54) LARGE SURFACE AREA TEMPERATURE SENSING DEVICE

(71) Applicant: CIRCA Scientific, Inc., Englewood, CO (US)

(72) Inventor: Shawn P. Fojtik, Park City, UT (US)

(73) Assignee: CIRCA Scientific, Inc., Englewood, CO (US)

(*) Notice: Subject to any disclaimer, the term of this patent is extended or adjusted under 35 U.S.C. 154(b) by 0 days.

(21) Appl. No.: 14/881,002

(22) Filed: Oct. 12, 2015

(65) Prior Publication Data

US 2016/0029897 A1 Feb. 4, 2016

Related U.S. Application Data

(63) Continuation of application No. 12/406,771, filed on Mar. 18, 2009, now Pat. No. 9,155,476.

(Continued)

(51) Int. Cl.
*A61B 5/01* (2006.01)
*A61B 34/20* (2016.01)
(Continued)

(52) U.S. Cl.
CPC ............ *A61B 5/015* (2013.01); *A61B 5/0036* (2018.08); *A61B 5/01* (2013.01); *A61B 5/4836* (2013.01);
(Continued)

(58) Field of Classification Search
CPC ......... A61B 5/015; A61B 5/01; A61B 5/6853; A61B 5/6858; A61B 2018/00797;
(Continued)

(56) References Cited

U.S. PATENT DOCUMENTS 2,756,752 A 7/1956 Scherlis
D237,116 S 10/1975 Ekbladh
(Continued)

FOREIGN PATENT DOCUMENTS

EP 1504725 A1 2/2005
JP HEI 01107307 U 7/1989
(Continued)

OTHER PUBLICATIONS

Korean Intellectual Property Office as International Searching Authority, "International Search Report and Written Opinion," dated Nov. 2, 2009, in international application No. PCT/US2009/037571.

(Continued)

*Primary Examiner* — Rene T Towa
(74) *Attorney, Agent, or Firm* — Dentons Durham Jones Pinegar (57) ABSTRACT

A temperature probe for monitoring temperatures of a surface of a tissue or organ within the body of a subject includes a section with a substantially two-dimensional arrangement and a plurality of temperature sensors positioned across an area defined by the substantially two-dimensional arrangement. Such an apparatus may be used in conjunction with procedures in which thermal techniques are used to diagnose a disease state or treat diseased tissue. Specifically, a temperature probe may be used to monitor temperatures across an area of a surface of a tissue or organ located close to the treated tissue to prevent subjection of the monitored tissue or organ to potentially damaging temperatures.

24 Claims, 5 Drawing Sheets

Related U.S. Application Data (60) Provisional application No. 61/037,624, filed on Mar. 18, 2008.

(51) Int. Cl.
*A61B 5/00* (2006.01)
*A61B 18/00* (2006.01)
*A61B 90/00* (2016.01)

(52) U.S. Cl.
CPC ............ *A61B 5/687* (2013.01); *A61B 5/6873* (2013.01); *A61B 5/742* (2013.01); *A61B 18/00* (2013.01); *A61B 34/20* (2016.02); *A61B 5/6853* (2013.01); *A61B 5/6858* (2013.01); *A61B 5/6859* (2013.01); *A61B 2018/00357* (2013.01); *A61B 2018/00404* (2013.01); *A61B 2018/00529* (2013.01); *A61B 2018/00547* (2013.01); *A61B 2018/00577* (2013.01); *A61B 2018/00797* (2013.01); *A61B 2034/2063* (2016.02); *A61B 2090/376* (2016.02); *A61B 2562/0271* (2013.01)

(58) Field of Classification Search
CPC .......... A61B 2562/0271; A61B 5/6859; A61B 34/20; A61B 5/742; A61B 5/4836; A61B 5/687; A61B 5/6873; A61B 18/00; A61B 2090/376; A61B 2034/2063; A61M 25/01; A61M 25/002
USPC ........................................... 600/549; 374/100
See application file for complete search history.

(56) References Cited

U.S. PATENT DOCUMENTS

| | | | |
|---|---|---|---|
| D282,965 S | 3/1986 | Wellenstam | |
| 4,676,249 A | 6/1987 | Arenas et al. | |
| 5,170,803 A | 12/1992 | Hewson et al. | |
| 5,211,183 A | 5/1993 | Wilson | |
| 5,325,848 A | 7/1994 | Adams et al. | |
| 5,382,231 A | 1/1995 | Shlain | |
| 5,391,155 A | 2/1995 | Sachse | |
| 5,536,274 A | 7/1996 | Neuss | |
| 5,673,695 A * | 10/1997 | McGee | A61B 5/0422 600/374 |
| 5,680,860 A * | 10/1997 | Imran | A61B 18/1492 600/374 |
| D389,365 S | 1/1998 | Lipson | |
| 5,800,413 A | 9/1998 | Swartz et al. | |
| 5,803,902 A | 9/1998 | Sienkiewicz et al. | |
| 5,807,339 A | 9/1998 | Boström et al. | |
| 6,015,382 A | 1/2000 | Zwart et al. | |
| 6,080,118 A | 6/2000 | Blythe | |
| 6,080,160 A * | 6/2000 | Chen | A61B 17/3468 128/897 |
| 6,090,050 A * | 7/2000 | Constantinides | A61B 5/015 374/100 |
| 6,106,522 A * | 8/2000 | Fleischman | A61B 5/0422 374/E1.005 |
| 6,371,928 B1 | 4/2002 | Mcfann et al. | |
| 6,406,442 B1 * | 6/2002 | McFann | A61B 17/221 600/434 |
| 6,432,041 B1 | 8/2002 | Taniguchi et al. | |
| 6,589,259 B1 | 7/2003 | Solingen | |
| 6,939,313 B2 * | 9/2005 | Saadat | A61B 5/015 600/587 |
| 7,140,766 B2 | 11/2006 | Glukhovsky et al. | |
| 7,293,915 B2 | 11/2007 | Chen | |
| 7,361,180 B2 | 4/2008 | Saadat et al. | |
| 7,621,908 B2 | 11/2009 | Miller | |
| D611,601 S | 3/2010 | Tamai et al. | |
| D624,651 S | 9/2010 | Leroy et al. | |
| D624,652 S | 9/2010 | Carus et al. | |
| D625,809 S | 10/2010 | Cuschieri et al. | |
| D625,812 S | 10/2010 | Dapri et al. | |
| D625,813 S | 10/2010 | Dapri et al. | |
| D626,226 S | 10/2010 | Carus et al. | |
| D626,227 S | 10/2010 | Leroy et al. | |
| 7,819,817 B2 * | 10/2010 | Rahn | A61B 5/01 600/549 |
| D650,076 S | 12/2011 | Dapri et al. | |
| D670,381 S | 11/2012 | Dapri et al. | |
| 9,155,476 B2 * | 10/2015 | Fojtik | A61B 5/015 |
| D758,574 S | 6/2016 | Fojtik | |
| 9,668,655 B2 | 6/2017 | Fojtik | |
| 9,744,339 B2 | 8/2017 | Fojtik | |
| 9,833,149 B2 | 12/2017 | Fojtik et al. | |
| 10,653,874 B2 | 5/2020 | Fojtik | |
| 2002/0133223 A1 | 9/2002 | Vito et al. | |
| 2003/0013985 A1 | 1/2003 | Saadat | |
| 2004/0073132 A1 | 4/2004 | Maahs et al. | |
| 2004/0133273 A1 | 7/2004 | Cox | |
| 2004/0176699 A1 | 9/2004 | Walker et al. | |
| 2004/0186469 A1 | 9/2004 | Woloszko et al. | |
| 2004/0215296 A1 | 10/2004 | Ganz et al. | |
| 2005/0033334 A1 | 2/2005 | Santra et al. | |
| 2005/0240116 A1 | 10/2005 | Saadat et al. | |
| 2006/0009715 A1 | 1/2006 | Khairkhahan et al. | |
| 2006/0085054 A1 * | 4/2006 | Zikorus | A61B 18/1492 607/96 |
| 2006/0106375 A1 | 5/2006 | Werneth et al. | |
| 2006/0116609 A1 | 6/2006 | Kanuka et al. | |
| 2006/0201519 A1 | 9/2006 | Frazier et al. | |
| 2006/0241564 A1 | 10/2006 | Corcoran et al. | |
| 2006/0282043 A1 | 12/2006 | Pyles | |
| 2006/0293697 A1 | 12/2006 | Nakao et al. | |
| 2007/0066968 A1 | 3/2007 | Rahn | |
| 2007/0118097 A1 | 5/2007 | Miller | |
| 2007/0118105 A1 | 5/2007 | Miller | |
| 2007/0135733 A1 | 6/2007 | Soukup et al. | |
| 2007/0179378 A1 * | 8/2007 | Boese | A61B 5/042 600/407 |
| 2007/0225701 A1 | 9/2007 | O'Sullivan | |
| 2007/0255183 A1 | 11/2007 | Chen | |
| 2008/0033415 A1 | 2/2008 | Rieker et al. | |
| 2008/0077126 A1 | 3/2008 | Rashidi | |
| 2008/0177175 A1 | 7/2008 | Mottola et al. | |
| 2008/0215047 A1 | 9/2008 | Calabro et al. | |
| 2008/0234606 A1 | 9/2008 | Itou | |
| 2008/0243112 A1 | 10/2008 | De Neve | |
| 2008/0272776 A1 | 11/2008 | Edelman | |
| 2008/0300590 A1 | 12/2008 | Horne et al. | |
| 2008/0306468 A1 | 12/2008 | Tamai et al. | |
| 2009/0030320 A1 | 1/2009 | Ishihara | |
| 2009/0112248 A1 | 4/2009 | Maloney | |
| 2009/0275956 A1 | 11/2009 | Burnes et al. | |
| 2009/0312602 A1 | 12/2009 | Sakamoto et al. | |
| 2010/0002916 A1 | 1/2010 | Yamaguchi | |
| 2010/0030098 A1 | 2/2010 | Fojtik | |
| 2010/0210944 A1 | 8/2010 | Kondo | |
| 2010/0312223 A1 | 12/2010 | Kozak et al. | |
| 2012/0010524 A1 | 1/2012 | Fojtik et al. | |
| 2012/0247530 A1 | 10/2012 | Dimov et al. | |

FOREIGN PATENT DOCUMENTS

| | | |
|---|---|---|
| JP | H02203835 A | 8/1990 |
| JP | HEI 03056048 B2 | 8/1991 |
| JP | H09-506069 A | 9/1997 |
| JP | 2002541905 A | 12/2002 |
| JP | 2005503241 A | 2/2005 |
| JP | 2005095602 A | 4/2005 |
| JP | 2005270425 A | 10/2005 |
| JP | 2007537784 A | 12/2007 |
| WO | 1995/0010318 A1 | 4/1995 |
| WO | 2000062699 A2 | 10/2000 |
| WO | 2002043789 A2 | 6/2002 |
| WO | 2005117755 A2 | 12/2005 |
| WO | 2006055286 A2 | 5/2006 |
| WO | 2007001981 A2 | 1/2007 |
| WO | 2009117523 A1 | 9/2009 |
| WO | 2012151584 A1 | 11/2012 |

(56) References Cited

FOREIGN PATENT DOCUMENTS

OTHER PUBLICATIONS

Merriam-Webster's Collegiate Dictionary 10th ed. Merriam-Webster, Inc. 2001. p. 449.
European Patent Office, "Supplementary European Search Report," in European Application No. 09721913.3, dated May 8, 2013.
United States Patent and Trademark Office Acting as the International Searching Authority, "International Search Report and Written Opinion," in international application No. PCT/US2011/036330, dated Aug. 16, 2011.
United States Patent and Trademark Office Acting as the International Searching Authority, "International Search Report and Written Opinion," in international application No. PCT/US2012/036814, dated Aug. 14, 2012.
Sine wave, Revision as of Nov. 7, 2006, [online], [retrieved on Dec. 14, 2010]. Retrieved from Internet ,<URL: http://www.wikipedia.org>.
File:Sine wave amplitude.svg, May 12, 2008, [online], [retrieved on Mar. 24, 2011]. Retrieved from Internet, <URL: http://www.wikipedia.org>.
Ralph M. Hartwell II, "An Improved Sine to Square Wave Convertor for Rife/Bare Systems," May 24, 2001, [online], [retrieved on Mar. 24, 2011], Retrieved from Internet, <URL: http://www.w5jgv.com>.
File:Waveforms.svg, Oct. 23, 2006, [online], [retrieved on Mar. 24, 2011]. Retrieved from Internet, <URL: http://www.wikipedia.org>.
Japanese Patent Office, "Final Notification of Reasons for Rejection," dated Dec. 19, 2014 in Japanese patent application No. 2013-510314.
Japanese Patent Office, "Reasons for Rejection," dated Feb. 27, 2015 in Japanese patent application No. 2014-103146.
European Patent Office, "Communication pursuant to Article 94(3) EPC," in European Application No. 09721913.3, dated Aug. 14, 2015.
Communication pursuant to Article 94(3) EPC from European Patent Office dated Feb. 7, 2017 in application No. 09 721 913.3-1666.
State Intellectual Property Office of the People's Republic of China, Notification of the First Office Action, CN App. No. 201711418339.3, dated Sep. 26, 2018.
State Intellectual Property Office of the People's Republic of China, Search Report, CN Application No. 201711418339.3, dated Sep. 26, 2018.
Japan Patent Office, Office Action, JP Application No. 2017-217984, dated Aug. 27, 2018.
Japan Patent Office, "Notice of Reasons for Refusal," Application No. JP2016-019544, dated Nov. 4, 2016.
European Patent Office, "Communication pursuant to Article 94(3) EPC," European Application No. 11781308.9, dated Dec. 4, 2017.
European Patent Office, "Communication pursuant to Article 94(3) EPC," European Application No. 11781308.9, dated Nov. 7, 2018.
European Patent Office, "Supplementary European Search Report," European Application No. 11781308.9, dated Nov. 5, 2014.
State Intellectual Property Office of the People's Republic of China, "Reexamination Decision," Chinese Application No. 201180031268.6, dated Sep. 25, 2017.
State Intellectual Property Office of the People's Republic of China, "Rejection Decision," Chinese Application No. 201180031268.6, dated Apr. 8, 2016.
State Intellectual Property Office of the People's Republic of China, "Fourth Office Action," Chinese Application No. 201180031268.6, dated Oct. 8, 2015.
State Intellectual Property Office of the People's Republic of China, "Third Office Action," Chinese Application No. 201180031268.6, dated Apr. 9, 2015.
State Intellectual Property Office of the People's Republic of China, "Second Office Action," Chinese Application No. 201180031268.6, dated Oct. 20, 2014.
State Intellectual Property Office of the People's Republic of China, "First Office Action," Chinese Application No. 201180031268.6, dated Mar. 5, 2014.
China National Intellectual Property Administration, "Rejection Decision," Chinese Application No. 201711418339.3, dated Feb. 25, 2020.
China National Intellectual Property Administration, "Third Office Action," Chinese Application No. 201711418339.3, dated Oct. 21, 2019.
China National Intellectual Property Administration, "Second Office Action," Chinese Application No. 201711418339.3, dated May 10, 2019.
Japan Patent Office, "Reasons for Rejection," Japanese Application No. 2020-184361, dated Sep. 29, 2021.
China National Intellectual Property Administration, "Board Opinion," Chinese Application No. 201711418339.3, dated Jun. 24, 2021.

* cited by examiner

LARGE SURFACE AREA TEMPERATURE SENSING DEVICE

CROSS-REFERENCE TO RELATED APPLICATIONS

This application is a continuation of U.S. patent application Ser. No. 12/406,771, filed on Mar. 18, 2009, titled LARGE SURFACE AREA TEMPERATURE SENSING DRIVE, now U.S. Pat. No. 9,155,476, issued Oct. 13, 2015, which claims the benefit of U.S. Provisional Patent Application No. 61/037,624, filed on Mar. 18, 2008, titled LARGE SURFACE AREA TEMPERATURE SENSING DEVICE. The entire disclosure of each of the forgoing patent applications is hereby incorporated herein.

TECHNICAL FIELD

The present invention relates generally to apparatuses for monitoring temperatures of an internal surface of a hollow organ in the body of a subject and, more specifically, to temperature monitoring apparatuses that are configured to monitor temperatures at different locations spread over an area of an internal surface of a hollow organ. The present invention also relates to methods in which temperatures across areas of an internal surface of a hollow organ are monitored, including techniques in which an adjacent tissue or organ is heated or cooled.

BACKGROUND OF RELATED ART

A variety of techniques have been developed in which tissues or organs in a patient's body are heated or cooled. Tissues may be heated by a variety of techniques, including high frequency ultrasound, radiofrequency treatments, laser treatments, use of infrared radiation, and by direct application of thermal energy. Cooling is often effected cryogenically. Techniques that heat and cool tissues may be collectively referred to as "thermal techniques."

Thermal techniques are useful for diagnosing a variety of disease states and for treating a variety of disease states. More specifically, thermal techniques may be used to diagnose and/or treat cancerous tissues, to destroy diseased tissues, to congeal blood, and to perform a variety of other diagnostic and surgical procedures. Examples of organs that may be subjected to thermal techniques include the heart, the lungs, gastrointestinal organs, the liver, the pancreas, urological organs, prostates, reproductive organs, and skin.

Figure 1:
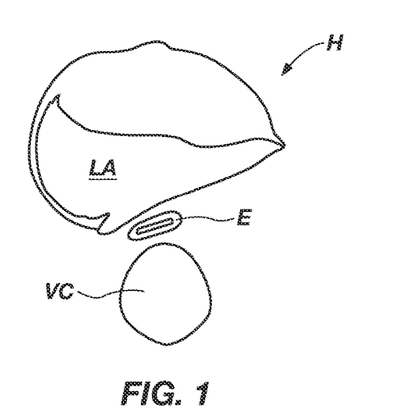
FIG. 1 is a cross-sectional representation of a portion of a human body illustrating the relationship between the esophagus and the heart.

The degree of heating or cooling that is required to optimize the efficiency of some thermal techniques may adversely affect tissues or organs that are adjacent to a treated tissue or organ. For example, a great deal of heat is generated when left atrial ablation techniques are used to treat atrial fibrillation in human subjects. In addition to heating and treating the diseased tissue in the heart H, the esophagus E, which is adjacent to the left atrium LA of the heart H, as shown in FIG. 1, may also be heated. As FIG. 1 illustrates, a typical human esophagus E typically has a narrow oval shape that resembles a pancake, with a large portion of the outer surface of the esophagus E located next to or in contact with the left atrium LA, although the size, shape, and/or position of the esophagus E may vary. In an average human adult, about 58 mm of the length and the majority of the front side of a 14 mm diameter esophagus E is located in proximity to or contacts the left atrium LA. As a consequence of this intimate arrangement between the esophagus E and the left atrium LA, the heat generated during left atrium ablation may damage the esophagus E and may, in some cases, create an esophageal fistula. Unfortunately, the complications that arise from esophageal fistula often do not present themselves until weeks after the procedure and, in many cases, at too late a time to treat and/or cure the sometimes fatal damage that has been done.

In recognition of the potentially dire consequences of overheating the esophagus E during left atrial ablation, some physicians have started using catheters with single temperature sensors to monitor the temperature within the subject's esophagus E. Typically, a catheter with a size of 9 French (about 3 mm diameter) to about 18 French (about 64 mm diameter) is used in conjunction with a conventional temperature sensor (e.g., an esophageal stethoscope available from Smiths Medical of Hythe, Kent, United Kingdom). If the sensed temperature reaches a predetermined level, the physician may discontinue the left atrial ablation momentarily to allow the esophagus E to cool. The effectiveness of these techniques is limited, however, as a single temperature sensor may only monitor heat at a single location within the relatively large area of the esophageal wall located adjacent to the left atrium LA.

In an apparent effort to reduce the likelihood of esophageal fistula during left atrial ablation procedures, a variety of different types of inflatable devices have been developed. Some inflatable devices are configured to cool the esophagus E during left atrial ablation. Other inflatable devices are configured to ensure contact between one or more temperature sensors and the interior surface of the front of the esophageal wall. Despite assertions to the contrary, since the esophagus E is confined between the left atrium LA of the relatively rigid heart H and the even more rigid vertebral column VC (see FIG. 1), any change in the shape of the esophagus E by inflating a device that has been introduced into the esophagus E merely pushes or distends the esophagus E closer to, or into more intimate contact with, the left atrium LA. The obvious result of such movement or distension is an increase in the likelihood that a left atrial ablation procedure will cause an esophageal fistula. In addition, use of an inflatable device will undesirably prevent a subject from swallowing during the typically lengthy (two to four hour) procedure, which may unnecessarily require that the subject be placed under general anesthesia during the procedure.

SUMMARY

The present invention includes various embodiments of temperature probes configured to be positioned against internal organ surfaces. A temperature probe that incorporates teachings of the present invention includes an elongate member and a plurality of temperature sensors carried at discrete locations along the length of the elongate member. When disposed within the interior of a hollow organ, a section of the elongate member is configured to have a substantially two-dimensional arrangement that arranges the temperature sensors in an area array. The arrangement of the shaped section of the elongate member is referred to as a "substantially two-dimensional arrangement" to account for the thicknesses of the elongate element and the temperature sensors carried thereby, as well as for any slight deviations of the elongate member from a desired plane for the two-dimensional arrangement.

A substantially two-dimensional arrangement of a portion of a temperature probe of the present invention may, in some embodiments, be defined during manufacture of the temperature probe or apparatus (e.g., catheters, guide wires, shaping wires, etc.) that are to be used therewith. In other embodiments, a temperature probe or an apparatus that is configured for use therewith may be configured to enable a physician to define the substantially two-dimensional arrangement.

In some embodiments, the elongate member comprises a flexible element with a section that, in a relaxed state, is pre-shaped to a desired, substantially two-dimensional arrangement. Elongate members with such characteristics may take on substantially linear, or one-dimensional, configurations when introduced into a linear catheter under stress but, upon removal of the pre-shaped section from the catheter, the pre-shaped section returns to its relaxed state, in which it has a substantially two-dimensional arrangement.

In other embodiments, the elongate member is an element that has a substantially linear, or one dimensional, configuration, but includes a section that may be formed into a substantially two-dimensional arrangement of desired configuration. A section of an elongate member that is ordinarily substantially linear may take on a substantially two-dimensional arrangement when a wire that includes a section with the substantially two-dimensional arrangement is introduced into a lumen of the elongate member. Such a wire may itself be somewhat flexible or selectively flexible (e.g., depending upon its temperature, etc.), and its introduction into the interior of a hollow organ of a subject's body may be enabled by rigidity of a proximal and/or intermediate portion of the elongate member, a property (e.g., shape memory, etc.) of the material from which the wire is formed, or by any other suitable means. When the shaped portion of the wire is introduced into a corresponding flexible section of the elongate member, that section of the elongate member may assume the substantially two-dimensional arrangement.

Other embodiments of temperature probes of the present invention include mechanisms for transforming substantially linear sections of elongate members to two-dimensional arrangements. In one such embodiment, an elongate element comprises a control wire, along with a multi-element portion along a portion of the length of the control wire. The multi-element portion includes at least two parallel arms that carry temperature sensors. While the multi-element portion is contained within a catheter, it may have a substantially linear configuration. Once the catheter has been introduced into the interior of a hollow organ, the control wire may be moved distally to push the multi-element portion out of a distal end of the catheter. The control wire may then be drawn back toward the distal end of the catheter, which engages an actuator associated with the at least two parallel arms and causes them to bow outwardly, forcing the multi-element portion into a substantially two-dimensional arrangement, such as a loop.

Other techniques for causing a section of a temperature probe to assume a substantially two-dimensional configuration (e.g., aspiration of air from a lumen extending through a section of the temperature probe, introduction of pressure into a lumen extending through a section of the temperature probe, manipulation of a section of a temperature probe following its introduction into the body of a subject, etc.) are also within the scope of the present invention.

The present invention includes techniques for introducing a temperature probe into the body of a subject with the temperature probe in a substantially linear, or one-dimensional, configuration, then allowing or causing a section of an elongate member of the temperature probe to assume the substantially two-dimensional arrangement when that section of the temperature probe is at a desired location within the subject's body.

In addition to including various embodiments of temperature probes, the present invention also includes embodiments of methods, or procedures, in which the temperatures at various locations over an area of a body tissue are monitored. When such a procedure is conducted, a first tissue or organ of a subject's body is subjected to a thermal technique while temperature is monitored over an area of an adjacent, second tissue or organ of the subject's body. In some embodiments, the temperature of the second tissue or organ may be monitored without substantial deformation of the second tissue or organ, without substantial displacement of the second tissue or organ, and/or without preventing the second tissue or organ from functioning. Additionally, if any portion of the monitored area approaches a potentially damaging (cold or hot) temperature, precautionary measures may be taken. Various embodiments of such precautionary measures include, but are not limited to, temporary termination of the thermal technique, movement of the affected portion of the second tissue or organ away from the first tissue or organ, and/or changing the temperature of the affected portion of the second tissue or organ.

In a specific embodiment, the method of the present invention may be effected during left atrial ablation, which is a surgical procedure that may be used to treat atrial fibrillation. During a left atrial ablation procedure, temperature may be monitored at a plurality of locations spaced over an area of an interior surface of a front portion of a subject's esophageal wall that is located adjacent to the left atrium of the subject's heart. Such temperature monitoring may be effected without any substantial change in the shape of the esophagus, without any substantial displacement of the monitored portion of the esophagus, and without blocking the esophagus or otherwise preventing the subject from swallowing. If any portion of the sensed area approaches a potentially damaging temperature, cautionary measures may be taken. In various embodiments, the left atrial ablation procedure may be temporarily terminated, the heated portion of the esophagus may be moved away from the left atrium, and/or the heated portion of the esophagus may be cooled.

Other embodiments of procedures in which thermal techniques are employed are also within the scope of the present invention, including, without limitation, monitoring the temperature of the trachea during ablation of the pulmonary vein; monitoring the temperature of the ureters and/or colon during thermal treatment of the prostate; monitoring the temperature of and, optionally, flattening a portion of the duodenum of the small intestine during thermal treatment of the liver (e.g., to treat hepatic carcinoma, etc.); monitoring the temperature of the cystic duct, gall bladder, and/or stomach during thermal treatment of the liver; monitoring brain temperature through tissues lining the nasal cavities; monitoring the temperature of tissues in the nasal cavities during thermal pharyngeal procedures; and monitoring tissues of or adjacent to the kidneys while breaking up kidney stones.

Other aspects, as well as various features and advantages, of the present invention will become apparent to those of ordinary skill in the art through consideration of the ensuing description, the accompanying drawings, and the appended claims.

DETAILED DESCRIPTION

Figure 2:
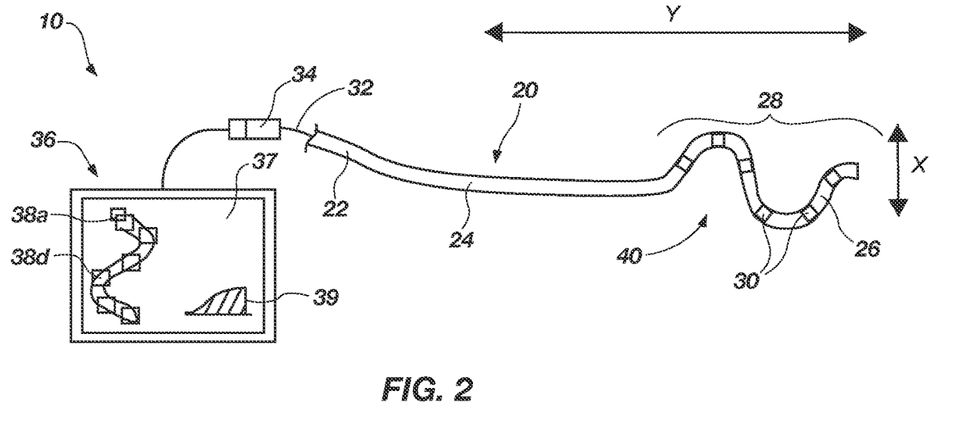
FIG. 2 depicts an embodiment of a temperature probe with an elongate member that includes a section with a substantially two-dimensional arrangement and temperature sensors arranged along the section of the elongate member in such a way that, when the section is in its substantially two-dimensional arrangement, the temperature sensors are arranged in an area array.

As shown in FIG. 2, a temperature probe 10 according to an embodiment of the present invention includes an elongate member 20 with a proximal portion 22, an intermediate portion 24, and a distal portion 26. In addition, temperature probe 10 includes a plurality of temperature sensors 30 located along one or both of intermediate portion 24 and distal portion 26. More specifically, temperature sensors 30 are positioned along a section 28 of elongate member 20 that is configured to have a substantially two-dimensional arrangement 40 when placed adjacent to or against an area of a surface of a tissue or organ in the body of a subject.

Section 28 may also carry other elements, such as radioopaque markers, echogenic markers, other sensors, and the like. The shape of the substantially two-dimensional arrangement 40 distributes three or more temperature sensors 30 over an area (e.g., an area array in the depicted embodiment) that is relatively large when compared with the miniscule area covered by elongate member 20 itself. Temperature sensors 30 may be arranged across an area array in which at least two temperature sensors 30 spaced laterally (x-axis X) apart from each other a first distance that exceeds a width of elongate member 20 and at least two temperature sensors 30 spaced vertically (y-axis Y) apart from each other a second distance that is at least as great as the first distance.

Elongate member 20 may, in various embodiments, have a length of about 20 cm to about 200 cm. The substantially two-dimensional arrangement 40 may have a width that exceeds a diameter of elongate member 20 by at least ten percent. In a specific embodiment, the substantially two-dimensional arrangement 40 covers an area with a width of about 10 mm to about 30 mm and a length of about 40 mm to about 80 mm, although substantially two-dimensional arrangements that cover narrower areas, wider areas, shorter areas, and longer areas are also within the scope of the present invention.

Figure 3:
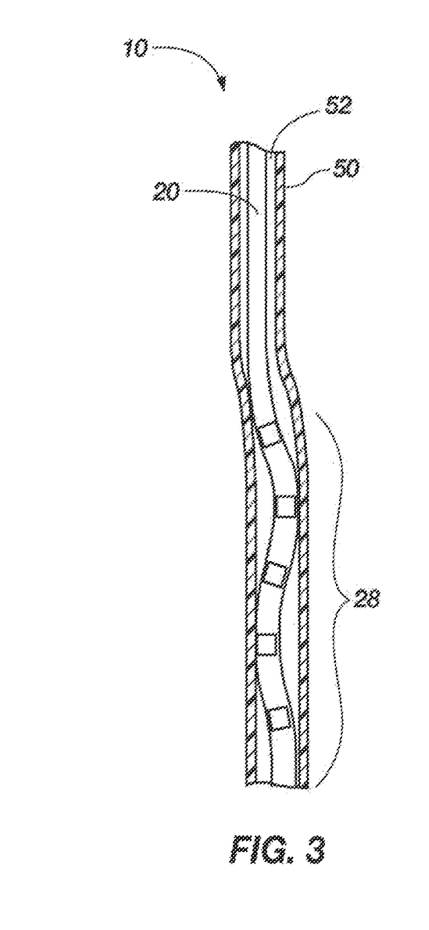
FIG. 3 illustrates the embodiment of temperature probe shown in FIG. 2, in a substantially linear, or one-dimensional, configuration when disposed within a lumen of a catheter having a substantially linear, or one-dimensional, configuration.

In some embodiments, such as that depicted by FIG. 2, section 28 of elongate member 20 may be configured in the substantially two-dimensional arrangement 40 while in a relaxed state. The material from which elongate member 20 is formed may, in such embodiments, be somewhat flexible and elastic, at least under certain conditions (e.g., when placed under a load, with or without other conditions), to enable elongation of section 28 from the substantially two-dimensional arrangement 40 to a more linear, substantially one-dimensional, configuration. For example, section 28 may be elongated when placed under a load within the lumen 52 of a catheter 50, as shown in FIG. 3.

A variety of materials are suitable for forming a preshaped but flexible elongate member 20 (or at least section 28 thereof), including plastics and metal alloys. In embodiments where section 28 of elongate member 20 is formed from a plastic, the plastic may comprise a polyester, a polyurethane, a latex, polyvinyl chloride, and the polyether block amide marketed as PEBAX®. Metals and/or metal alloys that may be used to form elongate member 20 include, but are not limited to, shape memory alloys such as the nickel-titanium alloy referred to as NITINOL (for nickel titanium naval ordinance laboratory), steel, nickel-titanium, cobalt-chromium, and the cobalt-based alloy available under the trade name ELIGLOY®. An elongate member 20 that is formed from a metal or metal alloy may, in some embodiments, be coated with a softer polymer to prevent damage to the tissues and organs of the body of a subject into which temperature probe 10 is introduced. In some embodiments, the entire elongate member 20 may be formed from the same material, while other embodiments of elongate member 20 have hybrid constructions, such as a metal proximal portion 22 joined to a plastic or shape memory alloy distal portion 26.

Figure 2A:
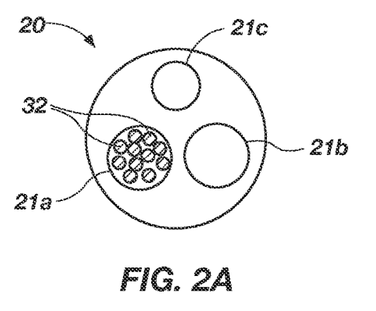
FIGS. 2A and 2B illustrate different embodiments of the elongate members of a temperature probe of the present invention.

As depicted by FIG. 2A, in some embodiments, including embodiments in which elongate member 20 is formed from a plastic, elongate member 20 may comprise a tubular member with one or more lumens 21a, 21b, 21c (three are shown) extending therethrough. Lumen 21a of such an elongate member 20 may be configured to accommodate wires (e.g., thermally conductive elements or electrically conductive wires 32 that lead to temperature sensors 30, to other sensors, etc.) or other elements of temperature probe 10. Lumen 21b may be configured to transport fluids into (e.g., fluids that provide a heat sink, cooled fluids to decrease a temperature of the sensed tissue, heated fluids to increase a temperature of the sensed tissue, etc.) or out of the subject's body, or to provide a pathway by which other medical devices may be introduced into the subject's body. Lumen 21c of elongate member 20 may be configured to receive a guide wire.

Figure 2B:
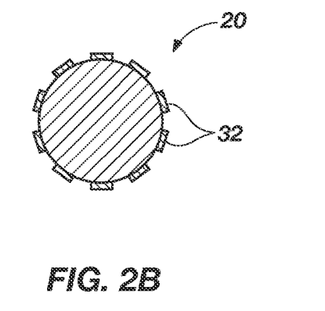

As an alternative to wires 32 that extend through an interior (e.g., through a lumen 21a) of elongate member 20, wires 32 may be carried upon an exterior of elongate member 20 (including embodiments in which elongate member 20 includes one or more lumens 21a, 21b, 21c, as well as embodiments in which elongate member 20 lacks lumens, or has a solid cross-section), as illustrated by FIG. 2B. Various embodiments of externally carried wires 32 include wires that are defined by etching a metal film formed on an external surface of elongate member 20, wires that are stamped or printed onto the external surface of elongate member 20, and wires that are discrete from, but carried by (e.g., wrapped around, etc.) the external surface of elongate member 20. Of course, in embodiments where elongate member 20 is formed from a metal or metal alloy, electrically insulative elements (e.g., a dielectric coating, etc.) (not shown) may electrically isolate wires 32 that are carried by the exterior surface of elongate member 20 from the material of elongate member 20.

As depicted by FIG. 2B, in some embodiments, elongate member 20 may have a solid cross section.

Each temperature sensor 30 of temperature probe 10 may comprise any suitable type of temperature sensor known in the art. In various embodiments, thermocouples or thermistors that have been swaged to metal or thermally conductive (e.g., platinum, platinum-iridium, gold, etc.) sensors may be used as temperature sensors 30. Each temperature sensor 30 may comprise a single element configured to detect a single temperature at a particular location. Alternatively, one or more temperature sensors 30 of a temperature probe 10 of the present invention may include a plurality of ganged temperature sensing elements, each of which may sense and/or report a different temperature to provide a more accurate temperature reading at a particular location.

Wires 32 that communicate with temperature sensors 30 (or with individual temperature sensing elements of a temperature sensor 30) extend proximally along elongate member 20 to a suitable connector 34 associated with proximal portion 22 of elongate member 20. In some embodiments, connector 34 may comprise a known 400 series connector or a known series 700 connector, such as, or similar to, those manufactured by Datex Ohmeda, GE Medical, Nihon Kohden, or Vital Signs, Inc.

Connector 34 enables connection of wires 32 and, thus, thermal sensors 30 to a suitable temperature monitor (not shown) that, in turn, communicates with a processing element (not shown) associated with a temperature display system 36. In the depicted embodiment, display system 36 includes a display element 37 that shows the temperatures 38a, 38b, etc., monitored at various locations that correspond to the locations of temperature sensors 30 in the substantially two-dimensional arrangement 40 of section 28 of elongate member 20. Temperatures 38a, 38b, etc., may be visually arranged in a manner that corresponds to the physical arrangement of temperature sensors 30 across the substantially two dimensional configuration 40. Additionally, display system 36 may clearly identify the warmest and coolest sensed temperatures 38a, 38b, etc. (e.g., by color, such as red and blue, respectively; by fast and slow flashing, respectively; etc.). Display system 36 may also present a rate 39 at which a sensed temperature is changing. The rate 39 of temperature change may be displayed numerically or, as depicted, graphically.

With reference to FIG. 3, an embodiment of a method for introducing a temperature probe 10 into a body of a subject is depicted. Specifically, temperature probe 10 is introduced into a lumen 52 of a substantially linear, or one-dimensional, catheter 50. Catheter 50 is sufficiently rigid to cause section 28 of elongate element 20 of temperature probe 10 to flex and, thus, to straighten while catheter 50 maintains its substantial linearity. In some embodiments, catheter 50 may also be sufficiently flexible to move through curved cavities or vessels. With the non-linear, substantially two-dimensional arrangement 40 (FIG. 2) of elongate element 20 of temperature probe 10 confined within lumen 52 of catheter 50 in a substantially linear configuration, temperature probe 10 may be easily introduced into a hollow area H within the body of a subject.

Figure 4:
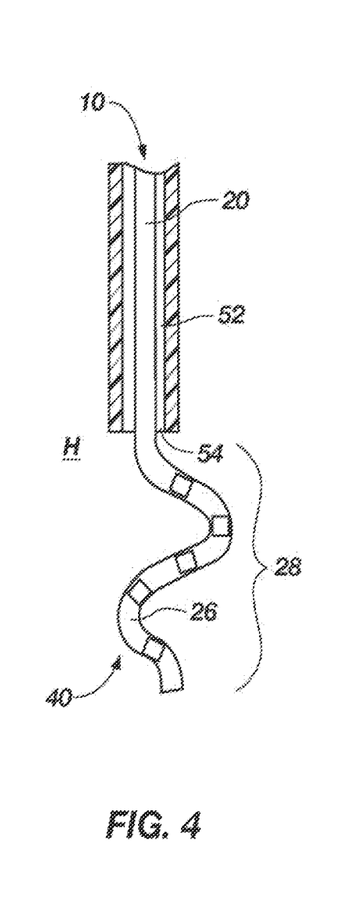
FIG. 4 depicts relaxation of a segment of the embodiment of temperature probe shown in FIG. 2 to its substantially two-dimensional arrangement upon exiting a distal end of the catheter of FIG. 3.

Once distal portion 26 of elongate element 20 of temperature probe 10 has been positioned within hollow area H, distal portion 26 and section 28 may be pushed out of a distal end 54 of lumen 52 and into hollow area H, where section 28 may assume its relaxed, substantially two-dimensional arrangement 40, as shown by FIG. 4.

As an alternative to the use of a catheter 50 to straighten temperature probe 10 and introduce a distal portion 26 of the same into hollow area H, a proximal end of a guide wire whose distal end has already been introduced into hollow area H may be introduced into a lumen 21c (FIG. 2A) of elongate member 30. The rigidity of the guide wire may be sufficient to straighten section 28 of elongate member 30, facilitating its introduction into hollow area H. Once section 28 has been introduced to a desired location, the guide wire may be removed from lumen 21c, allowing section 28 to assume the substantially two-dimensional arrangement 40.

Figure 5:
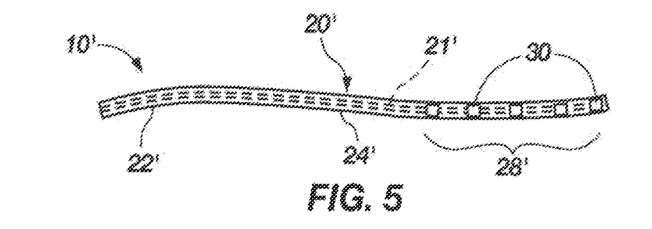
FIG. 5 shows an embodiment of a temperature probe with an elongate member that includes a flexible section that, in its relaxed state, may be substantially linear, or one-dimensional, and that includes a flexible section that carries a plurality of temperature sensors.

Another embodiment of temperature probe 10' of the present invention is depicted by FIGS. 5 through 9. As depicted by FIG. 5, temperature probe 10' comprises a substantially one-dimensional elongate member 20' with the same features as elongate member 20 (FIG. 2), with the primary exception being that section 28' of elongate member 20' is not shaped to have a substantially two-dimensional configuration 40 (FIG. 2). Instead, section 28' of elongate member 20' of temperature probe 10' is flexible, and may be deformed to take on a substantially two-dimensional configuration 40 (FIG. 2).

Figure 6:
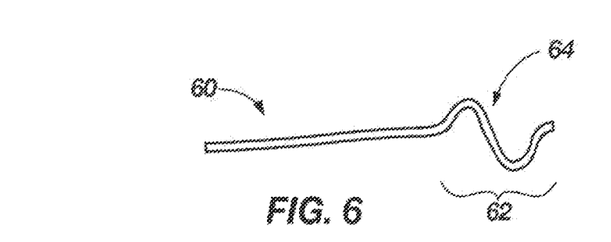
FIG. 6 illustrates an embodiment of a shaped wire with a section that, in its relaxed state, has a substantially two-dimensional arrangement.
Figures 7, 8:
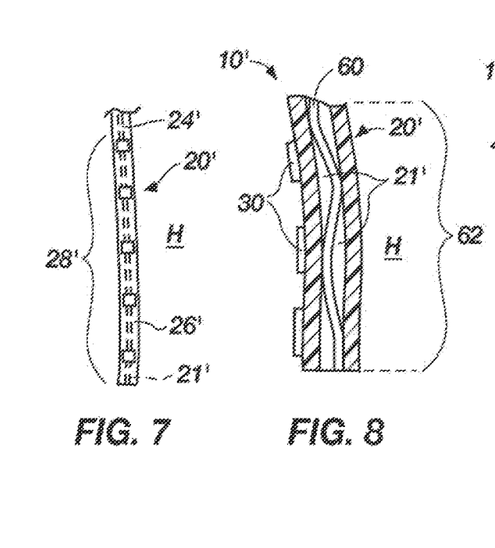
FIG. 7 depicts introduction of the embodiment of temperature probe shown in FIG. 5 into an interior of a hollow organ of a subject.
FIG. 8 depicts introduction of the shaped wire of FIG. 6 into the temperature probe of FIG. 5, with the section that has the substantially two-dimensional arrangement deformed to a substantially linear, or one-dimensional, configuration.

As depicted by FIGS. 6 and 7, a lumen 21' that extends through the length of elongate member 20' is configured to receive a shaped wire 60. As shown in FIG. 6, prior to its introduction into lumen 21', shaped wire 60 includes a section 62 that, in its relaxed state, has a substantially two-dimensional arrangement 64. Shaped wire 60 is a flexible element that may be substantially straightened. In various embodiments, shaped wire 60 may be formed from a somewhat rigid, yet flexible plastic or a metal or metal alloy, such as a shape memory alloy that is flexible at room temperature, but that becomes rigid when heated (e.g., to a subject's body temperature, etc.).

FIG. 7 illustrates the introduction of distal and intermediate portions 26' and 24' of elongate member 20' of temperature probe 10 into a hollow area H of the body of a subject. As elongate member 20' is introduced into hollow area H, so are temperature sensors 30 that are carried by section 28'. Due to its substantially linear, or one-dimensional configuration, known techniques may be used to introduce elongate member 20' into hollow area H.

Thereafter, shaped wire 60 may be introduced into lumen 21' of elongate member 20' of temperature probe 10', as illustrated by FIG. 8. As shaped wire 60 is introduced into lumen 21', section 62 of shaped wire 60 may be deformed (e.g., by the rigidity of a proximal portion 22' and/or intermediate portion 24' of elongate member 20' (FIG. 5), by temperature-dependent flexibility, etc.) to render section 62 substantially linear, or to have a one-dimensional configuration. Such deformation of section 62 enables shaped wire 60 to be easily introduced into a temperature probe 10' that has been inserted into hollow area H.

Figure 9:
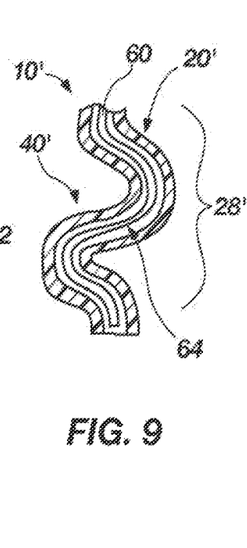
FIG. 9 shows the flexible section of the temperature probe of FIGS. 5 and 6 in substantially two-dimensional arrangement when the shaped portion of the wire of FIG. 6 assumes its substantially two-dimensional arrangement within the flexible section.

When section 62 (FIG. 6) of shaped wire 60 has been introduced into section 28' of elongate member 20' of temperature probe 10', section 62 may assume the substantially two-dimensional arrangement 64 (e.g., due to flexibility of section 28', upon being heated to or beyond a transition temperature, etc.), as depicted by FIG. 9. As section 62 of shaped wire 60 assumes the substantially two-dimensional arrangement 64, the flexibility of section 28' also allows it to be drawn into a corresponding, substantially two-dimensional arrangement 40'. With section 28' of elongate member 20' in the substantially two-dimensional arrangement 40', temperature sensors 30 (FIG. 5) that are carried by section 28' are spread across an area defined by the substantially two-dimensional arrangement 40'.

Figure 10:
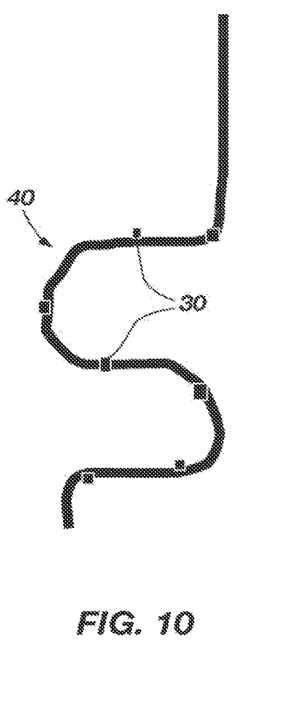
FIGS. 10 through 17 depict various embodiments of two-dimensional configurations in which a section of a temperature probe of the present invention may be arranged.
Figure 11:
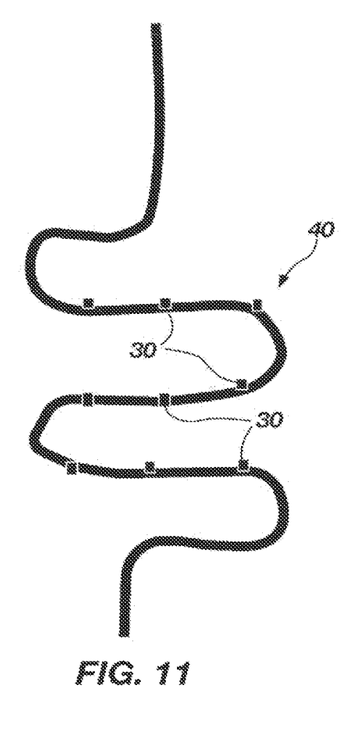
Figure 12:
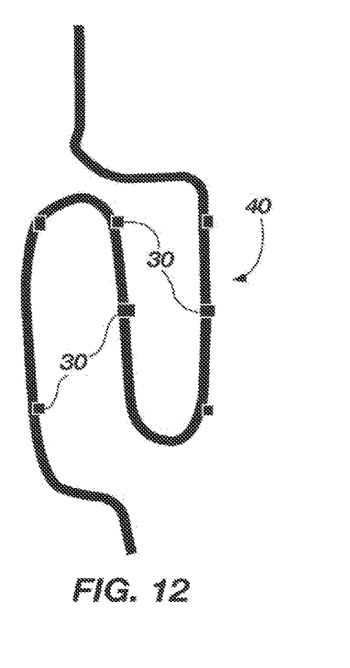
Figure 13:
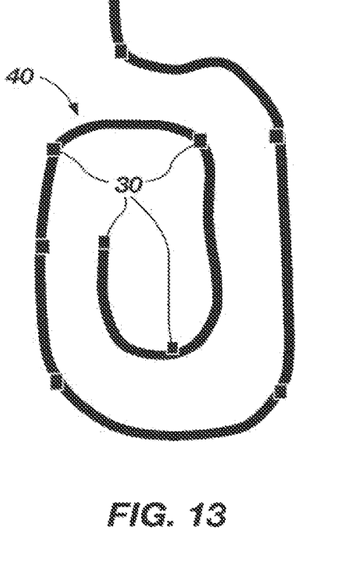
Figures 14, 15:
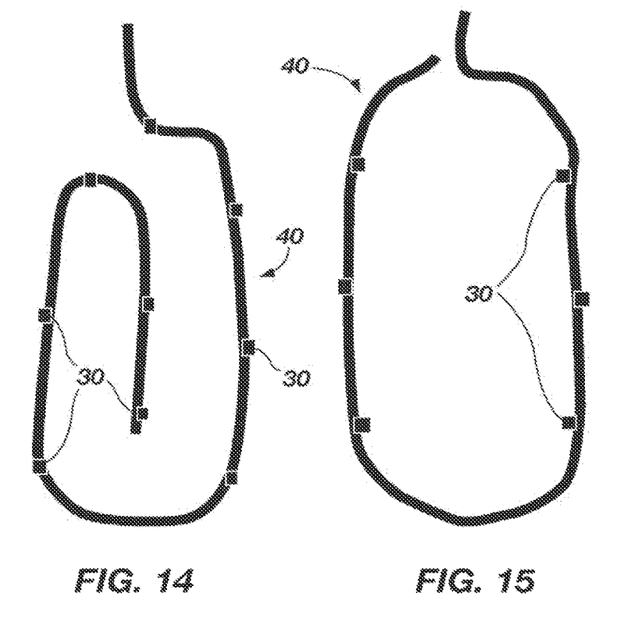
Figure 16:
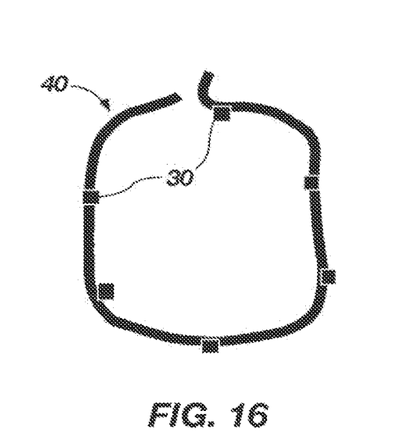

Referring now to FIGS. 10 through 16, various embodiments of substantially two-dimensional arrangements 40 are depicted along with possible arrangements of temperature sensors 30. Specifically, FIGS. 10 through 12 show different embodiments of serpentine, or S, arrangements, while FIGS. 13 and 14 depict examples of spiral, or pigtail, arrangements, and FIGS. 15 and 16 illustrate different looped arrangements. Of course, substantially two-dimensional arrangements 40 of other shapes and configurations are also within the scope of the present invention.

Figure 17:
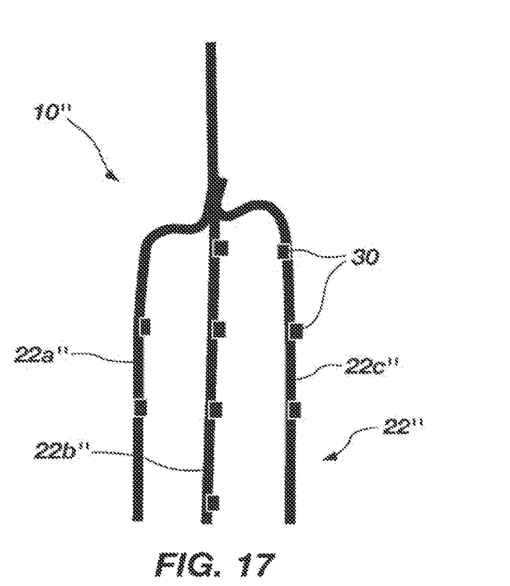

FIG. 17 illustrates a forked embodiment of temperature probe 10" with an enlarged distal portion 22" that includes two or more substantially parallel arms 22a", 22b", etc. (the depicted embodiment includes a distal portion 22" with three arms 22a", 22b", and 22c"). As illustrated, each arm 22a", 22b", and 22c" carries at least one temperature sensor 30. In some embodiments, one or more arms 22a", 22b", 22c", etc., may carry more than one temperature sensor 30.

Figure 18:
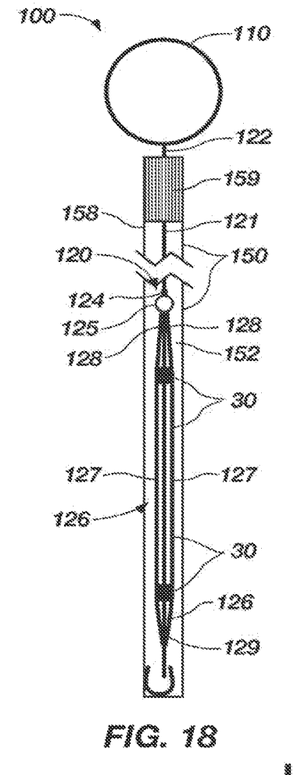
FIGS. 18 through 20 illustrate an embodiment of temperature probe configured to be mechanically arranged in a substantially two-dimensional arrangement upon being positioned at or near a desired location.
Figure 19:
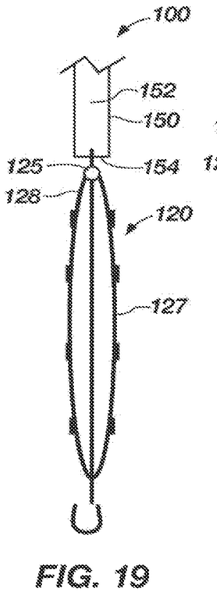
Figure 20:
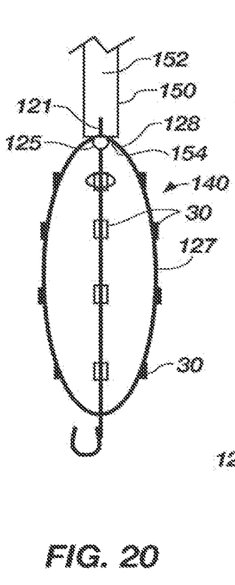

FIGS. 18 through 20 illustrate another embodiment of temperature probe 100, which is configured to be mechanically arranged in a substantially two-dimensional arrangement upon being positioned at or near a desired location.

As shown in FIG. 18, temperature probe 100 includes an introductory catheter 150, an elongate member 120 at least partially carried by introductory catheter 150, and a plurality of temperature sensors 30 carried by a distal portion 126 of elongate member 120.

Elongate member 120 includes a proximally located pull wire 121. A user engagement element 110 is associated with a proximal end 122 of pull wire 121 to facilitate movement of elongate member 120 through a lumen 152 of introductory catheter 150. Pull wire 121 may extend along substantially the entire length of elongate member 120. In the depicted embodiment, an intermediate portion 124 of pull wire 121 extends through a slip ring 125, to which proximal ends 128 of two or more loop wires 127 are secured. Each loop wire 127 carries at least one temperature sensor 30 and, as depicted, at least one loop wire 127 may carry a plurality of temperature sensors 30. Distal ends 129 of loop wires 127 are secured to pull wire 121 at or near its distal end 126. In some embodiments, distal ends 129 of loop wires 127 may be fixedly secured to pull wire 121.

Distal end 126 of pull wire 121 may be configured or covered with an element that prevents trauma to the tissues of a subject as pull wire 121 is advanced distally and distal end 126 exits introductory catheter 150.

In the arrangement shown by FIG. 18, loop wires 127 are contained within lumen 152 of introductory catheter 150. This arrangement facilitates the introduction of a distal portion of temperature probe 100 into a hollow area of a subject's body. Once the distal portion of temperature probe 100 has been placed at a desired location, elongate member 120 may be pushed distally through lumen 152 until proximal ends 128 of loop wires 127 and slip ring 125 have exited a distal end 154 of lumen 152 of introductory catheter 150, as depicted by FIG. 19.

Thereafter, as shown in FIG. 20, pull wire 121 may be proximally withdrawn. As pull wire 121 is proximally withdrawn, slip ring 125, proximal ends 128 of loop wires 127, and/or an engagement element (not shown) associated with slip ring 125 or with proximal ends 128 engage distal end 154 of introductory catheter 150. As pull wire 121 is further withdrawn and proximal ends 128 are held into place relative to distal end 154, loop wires 127 bow outwardly, providing a distal portion of temperature probe 100 with a substantially two-dimensional arrangement 140. While the distal portion of temperature probe 100 is in the substantially two-dimensional arrangement 140, temperature sensors 30 that are carried by loop wires 127 are spread across an area defined by the substantially two-dimensional arrangement 140. The area over which loop wires 127 spread depends, of course, upon the degree to which pull wire 121 is withdrawn.

With reference again to FIG. 18, user engagement element 110 and pull wire 121 may be associated with each other in such a way as to impart a user with control over an orientation of the substantially two-dimensional arrangement 140 (FIG. 20). In some embodiments, user engagement element 110 and pull wire 121 may be manipulated to enable deflection (e.g., of up to about 5°, etc.) of the substantially two-dimensional arrangement 140 in any direction relative to an axis of elongate member 120.

A position of pull wire 121 relative to introductory catheter 150 and, thus, the substantially two-dimensional arrangement 140 (FIG. 20) of the distal portion of temperature probe 100, may be maintained by causing a locking element 159 associated with a proximal end 158 of introductory catheter 150 to engage a proximal portion 122 of pull wire 121 (e.g., by screwing locking element 159 down into proximal portion 122, etc.).

Figure 21:
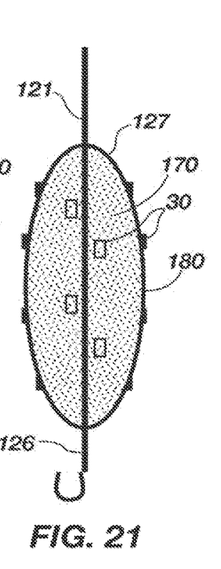
FIGS. 21 and 22 depict embodiments of temperature probes that include similar elements to the embodiment shown by FIGS. 18 through 20.
Figure 22:
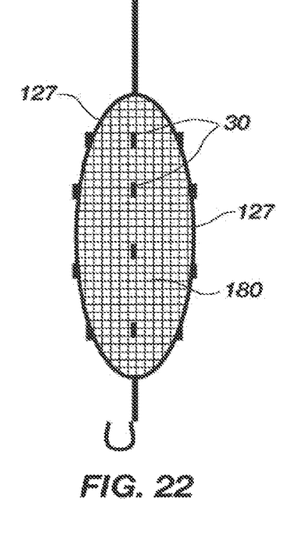

Instead of requiring that distal portion 126 of pull wire 121 be partially withdrawn into lumen 152 of introductory catheter 150 to expand loop wires 127, in other embodiments, a flexible element, such as a balloon 170 enclosed within a mesh basket 180 or a mesh basket 180 alone, may be secured to loop wires 127, as shown in FIGS. 21 and 22, respectively. Balloon 170 may be inflated by known techniques. Mesh basket 180 may comprise a compressed element that, when removed from lumen 152 of introductory catheter 150, automatically expands. Mesh basket 180 may have a substantially two-dimensional configuration (e.g., having a narrow oval, or pancake, cross-sectional shape, etc.) so as to minimize or even prevent manipulation of the shape, displacement, and/or blockage of the hollow organ within which either of these elements are placed. In embodiments including a balloon 170, mesh basket 180 may constrain the shape of the balloon 170 to the substantially two-dimensional configuration. In some embodiments, balloon 170 or mesh basket 180 may carry temperature sensors 30 until sufficient air pressure is added to balloon 170 to impart it with a more three-dimensional configuration.

Figure 23:
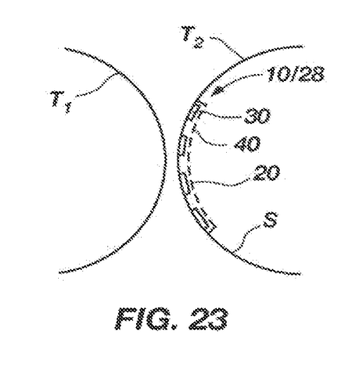
FIG. 23 schematically depicts use of an embodiment of a temperature probe of the present invention in conjunction with a procedure in which a thermal technique is employed.

With reference now to FIG. 23, an embodiment of a method, or procedure, is depicted in which an embodiment of temperature probe 10 of the present invention is used to monitor temperatures at a plurality of locations across an area of a surface S of second tissue or an organ $T_2$ in the body of a subject as a first tissue or organ $T_1$ of the subject's body is subjected to a thermal technique. A plurality of temperature sensors 30 distributed across an area defined by a substantially two-dimensional arrangement 40 of a section 28 of an elongate member 20 is placed against surface S. Section 28 may be placed against surface S without substantially deforming surface S or the shape of second tissue or organ $T_2$ of which surface S is a part, without substantially displacing any part of second tissue or organ $T_2$, and/or without preventing second tissue or organ $T_2$ from functioning properly as the temperature of surface S is monitored. In some embodiments, section 28 may deform slightly to conform to a shape of surface S.

If any portion of the monitored area of surface S approaches a potentially damaging (cold or hot) temperature, precautionary measures may be taken. Various embodiments of such precautionary measures include, but are not limited to, temporary termination of the thermal technique, changing the temperature of the affected portion of second tissue or organ $T_2$, and/or movement of the affected portion of second tissue or organ $T_2$ away from first tissue or organ $T_1$. Various embodiments for moving the affected portion of second tissue or organ $T_2$ include, but are not limited to, deformation of second tissue or organ $T_2$ to a flattened (e.g., narrowed oval) shape (e.g., by modifying an area occupied by the substantially two-dimensional arrangement 40 of section 28, etc.), manipulation of a position of temperature sensor 10 within the body of the subject to move a portion of second tissue or organ $T_2$, or any other suitable technique for moving tissue with temperature sensor 10.

Although the foregoing description contains many specifics, these should not be construed as limiting the scope of the present invention, but merely as providing illustrations of some embodiments. Similarly, other embodiments of the invention may be devised which lie within the scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed:

1. A temperature monitoring system, comprising:
   a temperature probe including: an elongate member having a longitudinal axis and including:
   a temperature sensing portion insertable into an interior of an esophagus of a subject, the temperature sensing portion being substantially two-dimensional and including a distal end, a proximal side opposite from the distal end, and a nonlinear arrangement, the nonlinear arrangement:
   defined by a series of bends in the elongate member that cause the elongate member to sequentially extend across the longitudinal axis at a series of locations from the proximal side toward the distal end,
   having a width of 14 mm to about 30 mm and a length that coincides with the longitudinal axis of the elongate member, and
   having sufficient flexibility to enable an entirety of the nonlinear arrangement to reversibly three-dimensionally deform to an area of an interior surface of a portion of the esophagus located adjacent to a left atrium of a heart of the subject as the nonlinear arrangement is positioned against the area of the interior surface of the portion of the esophagus; and
   a plurality of temperature sensors carried sequentially along a length of a distal portion of the elongate member so as to be arranged to make simultaneous contact with the interior surface of the portion of the esophagus by the distal portion of the elongate member when the distal portion is positioned against the area of the internal surface of the portion of the esophagus.

2. The temperature monitoring system of claim 1, wherein at least a portion of the temperature sensing portion of the elongate member of the temperature probe has a wave configuration.

3. The temperature monitoring system of claim 2, wherein the width of the temperature sensing portion of the elongate member of the temperature probe corresponds to a lateral (x-axis) distance between two laterally alternating portions of the wave configuration.

4. The temperature monitoring system of claim 2, wherein the wave configuration includes at least four alternating bends.

5. The temperature monitoring system of claim 4, wherein a distal end of the temperature sensing portion of the elongate member of the temperature probe, on a distal side of the temperature sensing portion, is substantially in-line with a proximal portion of the elongate member.

6. The temperature monitoring system of claim 1, wherein the width of the temperature sensing portion of the elongate member of the temperature probe corresponds to a distance between at least two adjacent bends of the temperature sensing portion.

7. The temperature monitoring system of claim 1, wherein the temperature sensing portion of the elongate member of the temperature probe has: a length that coincides with a remainder of a length of the elongate member; a width exceeding a width of the elongate member; and a thickness of about a same thickness of the elongate member and any additional elements carried by the temperature sensing portion of the elongate member.

8. The temperature monitoring system of claim 1, wherein the temperature sensing portion of the elongate member of the temperature probe is capable of being placed against and reversibly three-dimensionally deforming to a shape of an interior surface of the esophagus without substantially deforming the shape of the interior surface and/or without substantially displacing tissue of the esophagus.

9. The temperature monitoring system of claim 1, wherein a combined width of the temperature sensing portion of the elongate member of the temperature probe and the plurality of temperature sensors carried by the temperature sensing portion is capable of residing within the interior of the esophagus without substantially deforming a cross-sectional shape of the interior of the esophagus.

10. The temperature monitoring system of claim 1, wherein the plurality of temperature sensors of the temperature probe includes: at least two sensors spaced laterally (x-axis) apart from each other by a lateral (x-axis) distance that exceeds a diameter of the elongate member; and at least two sensors spaced longitudinally (y-axis) apart from each other a longitudinal (y-axis) distance that is at least as great as the lateral (x-axis) distance.

11. The temperature monitoring system of claim 1, further comprising: a catheter for introducing at least the temperature sensing portion of the elongate member of the temperature probe into the interior of the esophagus.

12. The temperature monitoring system of claim 11, wherein: the catheter includes a lumen that holds the temperature sensing portion of the elongate member of the temperature probe in a substantially linear configuration until the distal end of the temperature sensing portion of the elongate member is positioned at a desired location within an interior of a hollow organ; and at least a portion of the temperature sensing portion of the elongate member of the temperature probe, upon being withdrawn from the catheter, assumes the nonlinear arrangement.

13. The temperature monitoring system of claim 12, wherein at least the temperature sensing portion of the elongate member of the temperature probe comprises a preshaped flexible element constrained to the substantially linear configuration when positioned within the lumen of the catheter and to assume a substantially two-dimensional arrangement upon removal of the temperature sensing portion from the lumen of the catheter.

14. The temperature monitoring system of claim 1, wherein the area over which the nonlinear arrangement of the temperature sensing portion of the elongate member of the temperature probe extends is about 812 mm$^2$ to about 2,400 mm$^2$.

15. A temperature monitoring system, comprising: a temperature probe, comprising:
   an elongate member including a substantially two-dimensional portion with a nonlinear arrangement, an entirety of the nonlinear arrangement reversibly three-dimensionally deformable to a shape of an interior of a portion of an esophagus of a subject located adjacent to a left atrium of a heart of a subject when the entirety of the nonlinear arrangement is positioned against the interior of the portion of the esophagus, the nonlinear arrangement comprising a wave configuration having a length arranged along at least a portion of a longitudinal axis of the elongate member, the wave configuration comprising deviations from the longitudinal axis and having an amplitude that defines a width of the nonlinear arrangement, the width being about 14 mm to about 30 mm; and
   a plurality of temperature sensors carried sequentially along a length of the elongate member so as to be arranged by the wave configuration in an area array over the area of the interior of the portion of the esophagus located adjacent to the left atrium of the heart of the subject, the elongate member simultaneously placing the plurality of temperature sensors against the area of the interior of the portion of the esophagus.

16. The temperature monitoring system of claim 15, wherein the substantially two-dimensional portion of the elongate member of the temperature probe is preformed to have the nonlinear arrangement in a relaxed state.

17. The temperature monitoring system of claim 15, wherein the deviations of the wave configuration of the nonlinear arrangement of the substantially two-dimensional portion of the elongate member of the temperature probe include at least four alternating bends when the temperature probe is present within the interior of the esophagus of the subject.

18. The temperature monitoring system of claim 15, wherein a thickness of the substantially two-dimensional portion of the elongate member of the temperature probe is about the same as a diameter of the elongate member and any additional elements carried by the elongate member.

19. The temperature monitoring system of claim 15, wherein the entirety of the nonlinear arrangement of the substantially two-dimensional portion of the elongate member of the temperature probe can be positioned against the interior of the esophagus without substantially deforming a shape of the interior of the esophagus.

20. The temperature monitoring system of claim 15, wherein the entirety of the nonlinear arrangement of the substantially two-dimensional portion of the elongate member of the temperature probe can be positioned against the interior of the esophagus without substantially displacing tissue of the esophagus.

21. The temperature monitoring system of claim 15, wherein the entirety of the nonlinear arrangement of the substantially two-dimensional portion of the elongate member of the temperature probe can be positioned against the interior of the esophagus without substantially deforming a cross-sectional shape of the interior of the esophagus.

22. The temperature monitoring system of claim 15, wherein the area array of the plurality of temperature sensors of the temperature probe includes at least two sensors spaced laterally (x-axis) apart from each other across the width of the nonlinear arrangement a lateral (x-axis) distance that exceeds a diameter of the elongate member, and at least two sensors spaced longitudinally (y-axis) apart from each other a longitudinal (y-axis) distance that is at least as great as the lateral (x-axis) distance.

23. The temperature monitoring system of claim 15, wherein a distal end of the elongate member, on a distal side of the wave configuration, is substantially in-line with another portion of the elongate member proximal to the wave configuration of the substantially two-dimensional portion of the elongate member of the temperature probe.

24. The temperature monitoring system of claim 15, wherein the area of the nonlinear arrangement of the substantially two-dimensional portion of the temperature probe can extend is about 812 mm$^2$ to about 2,400 mm$^2$.

* * * * *